United States Patent [19]

Lengyel

[11] Patent Number: 4,617,049

[45] Date of Patent: Oct. 14, 1986

[54] METHOD FOR PROTECTING PLANT LIFE FROM ACIDIC ATMOSPHERIC POLLUTANTS

[76] Inventor: Albin D. Lengyel, 2417 E. Indian School Rd., Phoenix, Ariz. 85064

[21] Appl. No.: 768,062

[22] Filed: Aug. 22, 1985

[51] Int. Cl.$^4$ ............................................ A01N 43/16
[52] U.S. Cl. .......................................... 71/88; 71/81; 71/DIG. 1
[58] Field of Search ...................... 71/88, DIG. 1, 81

[56] References Cited

U.S. PATENT DOCUMENTS 4,336,052  6/1982  Chen et al. ...................... 71/DIG. 1

Primary Examiner—Catherine L. Mills
Attorney, Agent, or Firm—Drummond & Nissle

[57] ABSTRACT

A method for treating a stand of coniferous trees growing by natural processes and exposed to an atmosphere containing nitrogen pollutant compounds to improve the resistance of the trees to damage by acid rain. The method comprises the step of foliarly applying a sugar and source of potassium of magnesium to the coniferous trees growing in the stand of trees exposed to the atmosphere.

1 Claim, No Drawings

METHOD FOR PROTECTING PLANT LIFE FROM ACIDIC ATMOSPHERIC POLLUTANTS

This invention relates to a method for improving the resistance of a plant to atmospheric pollutants which either contact the foliage of the plant of contact the root system of the plant after being transported by rain into soil or into water reservoirs which are sources of minerals, water and other chemicals absorbed by the root system of the plant.

More particularly, the invention relates to a method for improving the resistance of a growing plant to atmospheric pollutants by providing the plant with chemical components which enable the plant to compensate for metabolic disorders caused when the atmospheric pollutants contact and are absorbed by the plant.

In another respect, the invention relates to a method for treating a stand of coniferous trees growing in an atmosphere containing nitrogen pollutant compounds to increase the resistance of the trees to the pollutant compounds.

So-called "acid rain" is believed to be a possible cause of the injury and death of many coniferous trees in the eastern United States and in the Black Forest of Germany, to name just a couple of areas that are noticeably effected. The pollutant components of acid rain include lead, cadmium and other heavy metals; ozone; iron; manganese; sulfuric acid; and nitric acid and other nitrogen pollutant components. The term "acid rain" is utilized to refer to atmospheric water droplets which include these pollutant chemicals and which either fall to the earth as rain droplets or are suspended in the atmosphere as a cloud. The concentration of pollutant chemicals in a cloud can be ten times greater than the concentration of the pollutant chemicals in precipitation. Accordingly, the effects of acid rain are often more pronounced on coniferous trees which grow near the summit of a mountain and are frequently surrounded by and saturated in cloud cover. In areas where the concentration of chemical pollutants in acid rain is high or where cloud cover containing chemical pollutants exists and saturates trees during extended periods of time, the needles on coniferous trees can turn variegated, yellow, bronze and eventually fall from the trees.

Extensive research has been performed on the effect of acid rain on forest ecosystems. Much of this research has centered on the effect of acid rain on forest soils. Some scientists question whether the recent die back of trees in the northeastern United States and in Germany can be attributed in whole or in part to acid rain. Other scientists believe acid rain is largely responsible for damage to coniferous stands of trees, but cannot agree upon an explanation of why the damage occurs, and, most importantly, have not demonstrated a process by which the resistance of coniferous forests to acid rain can be increased. See the report "Acid Precipitation in Relation to Agriculture, Forestry and Aquatic Biology", Council for Agricultural Science and Technology, 250 Memorial Union, Ames, Iowa 50011 (June, 1984).

In accordance with the invention, I have discovered a new method which effectively increases the resistance of coniferous trees and other plants to acid rain and atmospheric pollutants, particularly acidic nitrogen pollutants. My method comprises foliarly applying a sugar to plants. Sources of potassium and magnesium can also be applied to the plants. The sugar and sources of magnesium and potassium are presently preferably applied by preparing an aqueous solution of the sugar and sources of potassium and magnesium, and spraying it directly on the foliage of coniferous trees or other plants. The sugar and sources of potassium and magnesium can also be foliarly applied as powders, in combination with clay particles or other carrier particles, or by other foliar application methods known in the art.

While approximately twenty to forty pounds of sugar is utilized per acre of coniferous trees, any effective amount of sugar in the range of 1 to 300 pounds per acre can be foliarly applied to a stand of coniferous trees.

The sugar utilized in practicing the method of the invention can be fructose, glucose, galactose, sucrose or other monosaccharides, disaccharides, aldoses, ketoses or combinations thereof. Magnesium sulfate can be used as a source of magnesium. Potassium sulfate, potassium nitrate, potassium hydroxide, potassium chloride or potassium phosphates can be utilized as a source of potassium. Other sources of magnesium include magnesium carbonate as $MgCO_3$, $3MgCO_3.Mg(OH)_2.3H_2O$, $MgCO_3.3H_2O$, $MgCO_3.Mg(OH).3H_2O$, or $MgCO_3.5H_2O$; magnesium chloride, $MgCl_2$; magnesium chloride hexahydrate, $MgCl_2.6H_2O$; magnesium oxide, $MgO$; magne 3 sium peroxide, $MgO_2$; and magnesium orthophosphates.

In use, desired quantities of sugar are presently preferably dissolved in a volume of water. Potassium nitrate, potassium sulfate, potassium hydroxide, magnesium sulfate and other sources of magnesium and potassium can be added to the aqueous solution. The presently preferred mixture is thirty pounds of sucrose, twelve to fifteen pounds of potassium nitrate, sulfate or hydroxide and eight pounds of magnesium sulfate in twenty gallons of water. This mixture can be diluted as desired. The aqueous sugar-potassium-magnesium solution is foliarly applied to a stand of coniferous trees by aerial or ground spraying. The aqueous sugar solution is applied at ambient temperatures above, below or at 32° F. The volume of aqueous sugar solution applied to a stand of coniferous trees can vary as desired; however, approximately twenty to forty pounds of sugar is preferably generally evenly distributed over an acre of coniferous trees likely to be exposed to pollutant saturated cloud cover or already exhibiting the yellowing and bronzing of needles associated with acid rain. Any effective amount of sugar in the range of 1 to 300 pounds per acre of trees can be utilized. Five to fifteen pounds of magnesium sulfate is preferably generally uniformly applied over an acre of coniferous trees. Any effective amount of magnesium in the range of 1 to 300 pounds per acre can be utilized. Ten to twenty pounds of potassium nitrate, potassium sulfate or potassium hydroxide is generally uniformly applied over an acre of trees. Any effective amount of potassium in the range of 1 to 3,500 pounds per acre of coniferous trees can be utilized.

Although I do not wish to be bound by the following mechanism, according to my present understanding, it appears that a primary cause of the variegation, yellowing and bronzing of the needles on coniferous trees exposed to an acid rain atmosphere is nitric acid and other nitrogen pollutant chemicals. During summer, when the trees are actively growing and photosynthesis supplies an adequate supply of carbohydrates, nitric acid and other nitrogen pollutant chemicals absorbed by needles from acid rain contacting the needles provides additional nitrogen which increases the growth rates of the needles. When the metabolism and carbohydrate production of needles is markedly reduced in winter, the additional nitrogen supplied by acid rain contacting the trees disrupts the normal metabolism of the needles causing the needles, in essence, to attempt to grow without a proper supply of carbohydrates, i.e., of plant carbon. In addition, acid rain depletes the concentration of magnesium and potassium in the tree needles. Certain concentrations of these two minerals are essential for tree needles to withstand freezing temperatures. Consequently, a substantial amount of acid rain damage to coniferous trees occurs during winter. Application of the sugar solution of the invention supplies the needles of coniferous trees with an additional source of plant carbon which enables the needles to more nearly sustain a normal metabolism in the nitrogen rich atmospheric environment of acid rain.

I have also discovered that any available source of plant carbon can be foliarly applied to a naturally growing stand of coniferous trees and to other plants in combination with or in place of sugar to increase the resistance of the coniferous trees to nitrogen and other atmospheric pollutants contacting the trees; and, that sources of potassium and magnesium other than potassium nitrate, potassium sulfate, potassium hydroxide and magnesium sulfate can be applied to the needles of coniferous trees to increase the resistance of the trees to acid rain.

I have further discovered that applying a sugar or other source of plant carbon to soil and lake water reduces the injury which occurs to coniferous trees and other plants growing in the soil and to plants in the lakes when nitric acid and other atmospheric pollutants enter the soil and lake water. Sources of potassium and magnesium such as those earlier mentioned herein can also be applied to soil and lake water to reduce such injury.

As utilized herein, the term potassium sulfate refers to any water soluble potassium sulfate including $K_2SO_4$ and $K_2S_2O_7$; potassium nitrate refers to water soluble potassium nitrate; and magnesium sulfate includes $MgSO_4$ and epsom salts. As utilized herein the expression "water soluble" refers to chemicals which will partially or completely dissolve or decompose in water at at least one water temperature in the range between the freezing and boiling temperatures of water.

The following examples are presented, not by way of limitation of the scope of the invention, but to illustrate to those skilled in the art, the practice of various of the presently preferred embodiments of the invention and to distinguish the invention from the prior art.

EXAMPLE 1

Fourteen healthy potted Alderia pine trees and four healthy potted Mondale pine trees, each in a one gallon container of soil, were obtained and sequentially numbered. The Alderia pines were numbered 1 to 14; the Mondale pines 16 to 19. Each tree was approximately two feet tall. The needles on the lateral branches, at the terminals of the branches and on the trunks were green and healthy. An analysis of the chemical composition of needles on the trees was made. The results of the analysis are tabulated in Table 1.

The Alderia and Mondale pine trees were, over a period of fifty one (51) days, foliarly sprayed with aqueous nitrate and/or sugar solutions as described in Table 2.

Discussion

With reference to Table 2:

1. On Day 2 a slight variegation was evident on the older needles on the lateral branches of Alderia pine tree No. 4 near the base of the main stem or trunk. These older needles were yellowing. On Days 3 and 4, the variegation of Alderia No. 4 gradually became more marked and expanded to other needles. On Day 4, the nitrate concentration in the nitric acid spray applied to Alderia No. 4 was increased from 200 ppm (parts per million) to 800 ppm. By Day 7, Alderia No. 4 exhibited a definite yellowing and bronzing in the older needles on the lateral branches of the tree.

2. On the morning of Day 7 needles on Alderia No. 6 showed slight yellowing. On Day 7, needles on Alderia No. 7 also exhibited severe yellowing, initial bronzing, and reddish discolorations. The terminals of Alderia No. 7 were reddish and the growth of needles at the terminals appeared restricted. The yellowing, bronzing and reddening of needles are symptoms of magnesium deficiency. Alderia No. 5 remained green and exhibited no significant yellowing or variegation of the needles on Day 7.

3. By Day 9, the symptoms described above for Alderia pine trees Nos. 4, 6 and 7 had become more pronounced. Alderia No. 5 still did not exhibit any yellowing or damage as the result of application of the $NH_4NO_3$ spray. On Day 11, the concentration of $NH_4NO_3$ nitrates in the aqueous spray foliarly applied to Alderia No. 5 was increased to 800 ppm.

4. Alderia pine trees Nos. 8 to 11 were, as noted in Table 2, initially each sprayed once a day on Days 11 and 12 with an aqueous solution including sugar, potassium and magnesium. On Day 13 Alderia trees Nos. 8 to 11 were not sprayed with the nitrate solutions noted in Table 2. Also, on Day 11, Alderia No. 3 was renumbered Alderia No. 15, and aqueous sugar and aqueous nitrate solutions were applied thereto. Aqueous sugar and aqueous nitrate solutions were also simultaneously applied to Alderia Nos. 12 to 14 on Day 11.

5. On Days 13 and 14 Alderia Nos. 8 to 11 were sprayed with nitrate solutions. On the morning of Day 15, Alderia Nos. 8 to 11 did not exhibit yellowing or bronzing of the needles.

6. The application of nitrate sprays to Alderia Nos. 4-7 was discontinued on Day 14, and Alderia Nos. 4-7 were instead sprayed daily with an aqueous sugar-potassium-magnesium solution to evaluate the effectiveness of the sugar solution in promoting the recovery of Alderia damaged by nitrate solutions.

7. On Day 16, Mondale pine trees Nos. 16-19 were initially sprayed with nitrate solutions.

8. On Day 16, the health of Alderia Nos. 1, 2 and 4-15 was again observed:

(a) There was no significant change in Alderia Nos. 1, 2 and 4-7 except that the deterioration of Alderia Nos. 6 and 7 continued despite the continued daily applications of the sugar-potassium-magnesium solution which was initially applied on Day 14. Alderia Nos. 1 and 2 remained green and healthy.

(b) Alderia Nos. 8-10 exhibited yellowing and variegation of their needles, but to a lesser degree than did Alderia Nos. 4-6. Alderia Nos. 4-6 had been sprayed with nitrate solutions without first being sprayed with a sugar-potassium-magnesium aqueous solution. However, the yellowing and the bronzing of Alderia No. 11 was generally equivalent to that of Alderia No. 7 on Day 11, i.e., the initial application of sugar solution to Alderia No. 11 on Days 11 and 12 was not sufficient to help Alderia No. 11 in combating extremely high nitrate concentrations.

(c) Alderia Nos. 12 and 15 exhibited slight yellowing. There was no yellowing or variegation on Alderia No. 13. Alderia No. 14 exhibited slight yellowing and variegation.

9. On Day 16, applications of nitrate solutions were initiated on Mondale pine trees Nos. 16–19.

10. On Day 18, the condition of Alderia Nos. 1, 2 and 4–15 and of Mondale Nos. 16–19 was observed:

(a) The condition of Alderia Nos. 8 and 9 remained stable, but the condition of Alderia Nos. 10 and 11 had continued to deteriorate.

(b) The condition of Alderia Nos. 4 and 5 generally appeared stable. Alderia Nos. 6 and 7 had continued to deteriorate.

(c) Needles on Mondale Nos. 18 and 19 were beginning to bronze.

(d) Alderia Nos. 12 and 15 were not deteriorating.

11. On Day 22, the condition of trees 1, 2 and 4–19 was observed:

(a) Alderia No. 1 exhibited some bronzing of its lower needles, probably due to leaching of nitrogen by excessive watering.

(b) Alderia No. 2 remained green and was healthier than Alderia No. 1.

(c) Alderia No. 4 had yellowing, had no new growth, but had not deteriorated since Day 18.

(d) Alderia No. 5 exhibited no deterioration and was greener than Alderia No. 4. Alderia No. 5 had dense needles.

(e) The deterioration, yellowing and bronzing of the needles of Alderia No. 6 was continuing. The application of the sugar-potassium-magnesium solution was not halting deterioration.

(f) The deterioration of Alderia No. 7 was continuing. Only the outer one inch portion of each lateral branch remained green.

(g) Alderia No. 8 was stable, had dense needles and did not exhibit reddening of terminal buds.

(h) The deterioration, yellowing and bronzing of needles on Alderia No. 9 was continuing, but only at a slow rate.

(i) The deterioration of needles on the top lateral branches of Alderia No. 10 was slowing; however, needles on the lower lateral branches were continuing to bronze.

(j) Alderia No. 11 was continuing to deteriorate.

(k) Yellowing and bronzing was only occuring in the top lateral branches of Alderia No. 12 and was not evident in the remainder of the plant. The bottom portion of Alderia No. 12 was still dense and not exhibiting any yellowing, variegation or reddening of terminal buds. Yellowing was confined to the upper third of the plant.

(l) The bottom half of Alderia No. 13 was still dense. Only the top half of the plant had yellowing and bronzing needles.

(m) The condition of Alderia No. 14 was equivalent to that of Alderia No. 13.

(n) Alderia No. 15 remained green and dense with only slight yellowing and variegation which probably represented deterioration of needles in the plant which would normally occur even when the plant was not contacted with nitrate solutions.

(o) Yellowing and bronzing of needles was occuring on the lower main stem and bottom lateral branches of Mondale No. 16.

(p) The condition of Mondale No. 17 was similar to that of Mondale 16 with bronzing of needles occurring on the lower stem or trunk and not on the lateral branches or at the top of the plant.

(q) The condition of Mondale Nos. 18 and 19 was similar to that of Mondale No. 17, except the bronzing of needles extended further up the trunk and outwardly from the trunk along the lower lateral branches.

12. On Day 26, the condition of trees 1, 2 and 4–19 was observed:

(a) Alderia Nos. 1 and 2 were healthy and green. The number of bronze needles had slightly increased since Day 22.

(b) Alderia No. 4 was stable and in the same condition as on Day 22.

(c) Alderia No. 5 was green, had dense needles, and exhibited no signs of deterioration.

(d) Bronzing of needles was continuing to progress up the trunk and outwardly from the trunk along lateral branches toward the terminals of Alderia No. 6. There had been, since Day 22, no additional yellowing of needles. The bronzing was occurring on needles that had previously turned yellow. The outer one and a half to two inches of each lateral branch was green.

(e) Alderia No. 7 was continuing to deteriorate. Green needles existed in the tree only on the outer one-half to one inch of each lateral branch.

(f) Alderia No. 8 had not deteriorated further since Day 22 and had dense needles.

(g) The yellowing of the stem and lateral needles of Alderia No. 9 was continuing. The terminal buds were turning red.

(h) Necrosis of Alderia No. 10 was continuing at a slow rate. About 35% of the needles on the plant were yellowing or bronzing.

(i) Alderia No. 11 was continuing to deteriorate. Approximately 55% of the needles were yellowing or bronzing.

(j) Alderia No. 15 was healthy and had a beautiful distinct light green color.

(k) The upper portion of Alderia No. 12 was continuing to yellow. The bottom portion of the plant was still green and holding its own.

(l) The condition of Alderia No. 13 was generally equivalent to that of Alderia No. 12.

(m) Bronzing of needles was evident on about 75% of Alderia No. 14. The plant had definitely deteriorated since Day 22.

(n) The extent of bronzing of needles on Mondale No. 16 had continued to increase upwardly along the stem and outwardly from the stem along the lateral branches.

(o) The top of Mondale No. 17 was still green. The plant had experienced less bronzing and variegation than Mondale No. 16.

(p) The bronzing of needles on the stem had increased on Mondale No. 18. A minimal amount of bronzing had occurred on the lateral branches of the plant.

(q) Three-fourths of the needles on Mondale No. 19 had bronzed or begun to bronze. There was a minimal amount of yellowing of the needles.

13. On Day 31 the condition of trees 1, 2 and 4–19 was observed:

(a) The condition of Alderia No. 1 was generally equivalent to its conditions on Day 26. There were slightly more bronzed needles in the central older area of the plant.
(b) The condition of Alderia No. 2 was equivalent to that of Alderia No. 1 except that it was a paler green than Alderia No. 1.
(c) The condition of Alderia No. 4 was stable and had not deteriorated since Day No. 26. However, there was no new growth.
(d) The condition of Alderia No. 5 was stable and had not deteriorated since Day 26. The plant had dense needles and minimal yellowing and bronzing of the needles.
(e) The condition of Alderia No. 6 was equivalent to its condition on Day 26.
(f) Alderia No. 7 had continued to deteriorate.
(g) Alderia No. 8 was dense and green. The color of the plant had changed from a light green to a darker green. Bronzing of the needles was confined to portions of the lateral branches near the primary stem. The condition of Alderia No. 8 was generally equivalent to that of Alderia No. 5.
(h) Alderia No. 9 was still dense. Bronzing of the needles was confined to the lateral branches near the primary stem. Yellowing of needles had continued to slowly progress up the stem.
(i) Approximately 35% of the needles of Alderia No. 10 were yellowing.
(j) Alderia No. 11 had continued to deteriorate. Over 55% of the plant's needles were yellowing or bronzing.
(k) Alderia No. 12 was still green except for the upper six inch portion of the plant.
(l) The bottom of Alderia No. 13 was still green and dense. Only the top half of the tree exhibited yellowing or bronzing of needles.
(m) Alderia No. 14 had continued to deteriorate and was severely affected. 75% of the needles on the tree were yellow and/or bronze.
(n) The condition of Alderia No. 15 was equivalent to its condition on Day 26.
(o) The extent of bronzing of the needles of Mondale pine tree No. 16 had continued to expand up the stem and outwardly along the inner laterals of the tree.
(p) The condition of Mondale No. 17 was similar to that of Mondale No. 16. Fewer needles were bronzed on Mondale No. 17 than on Mondale No. 16.
(q) Needles were bronzed one-half of the way up the trunk of Mondale No. 18. Needles on the inner lateral branches were also affected.
(r) Needles were bronzed three-fourths of the way up the stem of Mondale No. 19.

An analysis of the chemical composition of the needles on Alderia pine trees Nos. 4–6 was performed on needles taken from the trees on Day 15 *after* the foliar spray application of the aqueous $HNO_3$ and $NH_4NO_3$ solutions had been discontinued and *prior* to the foliar application on Day 15 of the (CHO+K+Mg) aqueous solution. The results of this analysis are shown in Table 3.

An analysis of the chemical composition of the needles on each pine tree Nos. 1, 2 and 4–19 was performed after completion of the fifty-one (51) day spray schedule summarized in Table 2. The results of the analysis are summarized in Table 4.

As noted in Table 2, after Day 31 spray treatments were continued on an intermittent basis. However, the physical condition of pine trees 1, 2 and 4–19 on Day 31 generally corresponded to that of the trees on Day 51.

EXAMPLE 2

Four healthy potted Alderia pine trees, each in its own container of soil, are obtained and sequentially numbered 20 to 23. Each tree is approximately two feet tall. The needles on the lateral branches, at the terminals of the branches and on the trunks are green and healthy. An analysis of the chemical composition of needles on the trees is made. The results of the analysis are similar to those shown for Alderia pines Nos. 1-5 in Table 1.

Alderia Nos. 20–23 are subjected to a foliar spray treatment schedule identical to that shown in Table 2 for Alderia Nos. 4–7, except that Alderia Nos. 20–23 are sprayed with an aqueous sugar solution which contains only sucrose and does not contain sources of potassium and magnesium. Alderia No. 20 is sprayed in accordance with the schedule shown in Table 2 for Alderia No. 4; Alderia No. 21 is sprayed in accordance with the schedule shown in Table 2 for Alderia No. 5; Alderia No. 22 is sprayed in accordance with the schedule for Alderia No. 6; and, Alderia No. 23 is sprayed in accordance with the schedule for Alderia No. 7. Alderia 20-23 react to the aqueous sugar solution spray treatment in a manner which is generally equivalent to the reaction of Alderia Nos. 4–7 to the spray treatment schedule of Table 2.

EXAMPLE 3

Four healthy potted Alderia pine trees, each in its own container of soil, are obtained and sequentially numbered 24–27. Each tree is approximately two feet tall. The needles on the lateral branches, at the terminals of the branches and on the trunks are green and healthy. An analysis of the chemical composition of needles on the trees is made. The results of the analysis are similar to those shown for Alderia pines Nos. 1-5 in Table 1.

Alderia Nos. 24–27 are subjected to a foliar spray treatment schedule identical to that utilized for Alderia Nos. 20-23 in Example 2, except that Alderia Nos. 24–27 are sprayed with an aqueous sugar solution which contains fructose instead of sucrose. Alderia No. 24 is sprayed in accordance with the schedule for Alderia No. 20; Alderia No. 25 in accordance with the schedule for Alderia No. 21; Alderia No. 26 in accordance with the schedule for Alderia No. 22; and, Alderia No. 27 in accordance with the spray schedule for Alderia No. 23. Alderia 24–27 react to this aqueous sugar solution spray schedule in a manner which is generally equivalent to the reaction of Alderia Nos. 20-23 to the spray treatment of Example 2.

EXAMPLE 4

Four healthy potted Alderia pine trees, each in its own one gallon container of soil, are obtained and sequentially numbered 28 to 31. Each tree is approximately two feet tall. The needles on the lateral branches at the terminals of the branches and on the trunks are green and healthy. An analysis of the chemical composition of needles on the trees is made. The results of the analysis are similar to that shown for Alderia pines Nos. 1-5 in Table 1.

Alderia Nos. 28–31 are subjected to a foliar spray treatment schedule identical to that utilized for Alderia Nos. 20-23 in Example 2, except that Alderia Nos. 28-31 are sprayed with an aqueous sugar solution which contains fructose instead of sucrose. Alderia No. 28 is sprayed in accordance with the schedule for Alderia No. 20; Alderia No. 29 in accordance with the schedule for Alderia No. 21; Alderia No. 30 in accordance with the schedule for Alderia No. 22; and, Alderia No. 31 in accordance with the spray schedule for Alderia No. 23. Alderia 28–31 react to this aqueous sugar solution spray schedule in a manner which is generally equivalent to the reaction of Alderia Nos. 20–23 to the spray treatment of Example 2.

EXAMPLE 5

The procedure of Example 2 is repeated, except that Palmitic Acid is utilized in place of sucrose. Similar results are obtained.

EXAMPLE 6

The procedure of Example 2 is repeated, except that Stearic Acid is utilized in place of sucrose. Similar results are obtained.

TABLE 1
ANALYSIS OF HEALTHY NEEDLES ON ALDERIA AND MONDALE PINE TREES PRIOR TO THE FOLIAR SPRAY OF THE TREES AS DESCRIBED IN TABLE 2

| TREES | $NO_3$—N | TOTAL % N | TOTAL % P | % K | % Na | % Mg | Mn ppm | Zn ppm | Fe ppm | Cu ppm | % Ca |
|---|---|---|---|---|---|---|---|---|---|---|---|
| ALDERIA PINES Nos. 1–3 | 155 | 1.6 | 0.124 | 1.26 | 0.28 | 0.31 | 155 | 48 | 90 | 7 | 0.48 |
| ALDERIA PINES Nos. 4 & 5 | 146 | 1.6 | 0.120 | 1.51 | 0.20 | 0.26 | 141 | 46 | 98 | 6 | 0.44 |
| MONDALE PINES Nos. 16–19 | 293 | 1.3 | 0.132 | 0.82 | 0.22 | 0.29 | 129 | 38 | 92 | 14 | 0.50 |

NOTES:
1. Values in Table represent averages.
2. All percentages are weight percentages.
3. Alderia pines 6–14 purchased at same nursery as trees 1–5 one week after trees 1–5 were purchased. Each tree 1–14 was in generally the same healthy condition; consequently, the mineral composition of the needles of trees 6–14 at the time of purchase is believed to have been generally equivalent to that indicated above for trees 1–5.

TABLE 2
SUMMARY OF SPRAY TREATMENTS FOLIARLY APPLIED TO ALDERIA AND MONDALE PINES DURING 51 DAY TEST PERIOD

| TREE NO. | DAYS 1–3 | DAYS 4, 5 | DAYS 6–10 | DAYS 11, 12 | DAY 13 | DAYS 14, 15 | DAYS 16–31 | DAYS 32–51 |
|---|---|---|---|---|---|---|---|---|
| 1 | Water | ← | ← | ← | $H_2O$ Con't→ | → | → | → |
| 2 | CHO | ← | ← | ← | CHO Con't→ | → | → | → |
| 3 | CHO | ←CHO Con't→ | | Renumbered as Tree No. 15 | | | | |
| 4 | 200 ppm nitrate as $HNO_3$ | 800 ppm nitrate as $HNO_3$ | ← | $HNO_3$ Con't | → | Stopped $HNO_3$; Began (CHO+K+Mg) | ←(CHO+K+Mg Con't)→ | |
| 5 | 200 ppm nitrate as $NH_4NO_3$ | ←$NH_4NO_3$ Con't→ | | 800 ppm ← nitrate as $NH_4NO_3$ | Con't $NH_4NO_3$ | Stopped $HN_4NO_3$; Began (CHO+K+Mg) | ←(CHO+K+Mg Con't)→ | |
| 6 | ←No Treatment→ | | 5000 ppm nitrate as $HNO_3$ | ←$HNO_3$ Con't | → | Stopped $HNO_3$; Began (CHO+K+Mg) | ←(CHO+K+Mg Con't)→ | |
| 7 | ←No Treatment→ | | 10,000 ppm nitrate as $HNO_3$ | ←$HNO_3$ Con't | → | Stopped $HNO_3$; Began (CHO+K+Mg) | ←(CHO+K+Mg Con't)→ | |
| 8 | ←No Treatment→ | → | | Began (CHO+K+Mg) | Stopped (CHO+K+Mg); Began 800 ppm nitrate as $NH_4NO_3$ | ← | Con't $NH_4NO_3$ | → |
| 9 | ←No Treatment→ | → | | Began (CHO+K+Mg) | Stopped (CHO+K+Mg); Began 800 ppm $HNO_3$ | ← | Con't $HNO_3$ | → |
| 10 | ←No Treatment→ | → | | Began (CHO+K+Mg) | Stopped (CHO+K+Mg); Began 5000 ppm $HNO_3$ | ← | Con't $HNO_3$ | → |
| 11 | ←No Treatment→ | → | | Began (CHO+K+Mg) | Stopped (CHO+K+Mg); Began 10,000 ppm $HNO_3$ | ← | Con't $HNO_3$ | → |
| 12 | ←No Treatment→ | → | | Began (CHO+K+Mg) with 800 ppm nitrate as $HNO_3$ | ← | ←Con't Combined→ Sugar-nitrate | | → |
| 13 | ←No Treatment→ | → | | Began (CHO+K+Mg) with 5000 ppm nitrate as $HNO_3$ | ← | ←Con't Combined→ Sugar-nitrate | | → |

TABLE 2-continued

SUMMARY OF SPRAY TREATMENTS FOLIARLY APPLIED TO ALDERIA AND MONDALE PINES DURING 51 DAY TEST PERIOD

| TREE NO. | DAYS 1-3 | DAYS 4, 5 | DAYS 6-10 | DAYS 11, 12 | DAY 13 | DAYS 14, 15 | DAYS 16-31 | DAYS 32-51 |
|---|---|---|---|---|---|---|---|---|
| 14 | ←No Treatment→ | | → | Began (CHO+K+Mg) with 10,000 ppm nitrate as $HNO_3$ | ← | ←Con't Combined→ Sugar-nitrate | | → |
| 15 | ←No Treatment→ | | → | Began (CHO+K+Mg) with 800 ppm nitrate as $NH_4NO_3$ | ← | ←Con't Combined→ Sugar-nitrate | | → |
| 16 | ← | ← | ←No Treatment→ | | → | → | Began 800 ppm nitrate as $HNO_3$ | ←Con't→ $HNO_3$ |
| 17 | ← | ← | ←No Treatment→ | | → | → | Began 800 ppm nitrate as $NH_4NO_3$ | Con't spray $NH_4NO_3$ |
| 18 | ← | ← | ←No Treatment→ | | → | → | Began 5000 ppm nitrate as $HNO_3$ | Con't spray $HNO_3$ |
| 19 | ← | ← | ←No Treatment→ | | → | → | Began 10,000 ppm nitrate as $HNO_3$ | Con't spray $HNO_3$ |

NOTES:
1. Each chemical noted above was in aqueous solution sprayed on particular trees on the days noted in Table 2. For example, "5000 ppm nitrate as $HNO_3$" indicates an aqueous solution of $HNO_3$ having 5000 ppm $NO_3$.
2. Rate of application of sprays: (a) During Days 1-51 the appropriate spray solution was foliarly applied to each tree three times daily, except for the (CHO+K+Mg) sprays initiated on trees 4-7 on Day 14 and on trees 8-11 on Day 11. The (CHO+K+Mg) sprays were applied to trees 4-7 and 8-11 only once a day.
3. Coverage of spray solution: (a) 90%+ of the needles on a tree were wetted when a spray solution was applied to the tree; (b) each time a tree was sprayed a generally equivalent volume of the appropriate spray solution identified in Table 2 was utilized.
4. Composition of spray solutions: (a) The aqueous CHO solution utilized to spray trees Nos. 2 and 3 beginning on Day 1 comprised 31 grams sugar per .30 ml of water; (b) the aqueous (CHO+K+Mg) noted above comprised 0.24 grams of sugar, 0.12 grams of potassium nitrate, and 0.08 grams of magnesium sulfate per ml of water; and, (c) each $HNO_3$ or $NH_4NO_3$ solution noted above comprised a volume of water having the ppm of nitrate noted in Table 2. For example, 800 pm nitrate as $HNO_3$ consists of an aqueous nitric acid solution having 800 ppm nitrate.
5. The soil in each one gallon tree container was periodically watered as necessary.
6. Trees 1-15 were Alderia pine trees. Trees 16-19 were Mondale pine trees.
7. All spray solutions were foliarly applied at an ambient temperature of 50-90° F.
8. In TABLE 2 and in the above notes, CHO is used as a shorthand designation for sugar. The CHO or sugar utilized in the spray treatments outlined by TABLE 2 was sucrose, $C_{12}H_{22}O_{11}$.

TABLE 3

ANALYSIS OF NEEDLES ON ALDERIA PINE TREES NOS. 4 to 7 AFTER FOLIAR SPRAY APPLICATION OF AQUEOUS $HNO_3$ AND $NH_4NO_3$ SOLUTIONS WERE DISCONTINUED ON DAY 15 (SEE TABLE 2) AND PRIOR TO INITIAL FOLIAR SPRAY APPLICATION OF (CHO + K + Mg) SPRAY SOLUTION

| TREE NO. | $NO_3$—N | TOTAL % N | TOTAL % P | % K | % Na | % Mg | Mn ppm | Zn ppm | Fe ppm | Cu ppm | % Ca |
|---|---|---|---|---|---|---|---|---|---|---|---|
| 4 | 537 | 2.26 | .144 | 1.02 | .22 | .25 | 136 | 22 | 22 | 6 | .28 |
| 5 | 482 | 2.21 | .148 | .80 | .21 | .19 | 121 | 33 | 33 | 5 | .16 |
| 6 | 2200 | 2.70 | .156 | .98 | .19 | .17 | 126 | 27 | 27 | 4 | .19 |
| 7 | 4400 | 2.80 | .140 | .79 | .19 | .20 | 110 | 30 | 30 | 5 | .22 |

NOTES:
1. All percentages are weight percentages. For example, the numerical values under the column headed % K indicate the weight percent of potassium in the needles of the appropriate tree.

TABLE 4

ANALYSIS OF NEEDLES ON EACH ALDERIA AND MONDALE PINE TREE NOS. 1, 2 and 4-19 AFTER COMPLETION OF FOLIAR SPRAY TREATMENT SCHEDULE OF TABLE 2

| TREE NO. | $NO_3$—N | TOTAL % N | TOTAL % P | % K | % Na | % Mg | Mn ppm | Zn ppm | Fe ppm | Cu ppm | % Ca |
|---|---|---|---|---|---|---|---|---|---|---|---|
| 1 | 146 | 1.61 | .136 | 1.63 | .16 | .24 | 155 | 66 | 225 | 12 | .34 |
| 2 | 155 | 1.60 | .108 | 1.78 | .22 | .25 | 119 | 52 | 82 | 6 | .34 |
| 3 | (see Tree 15) | | | | | | | | | | |
| 4 | 247 | 1.89 | .136 | 1.41 | .29 | .25 | 143 | 38 | 90 | 5 | .28 |
| 5 | 258 | 1.69 | .128 | 1.68 | .25 | .28 | 149 | 33 | 101 | 4 | .34 |
| 6 | 403 | 2.00 | .152 | 1.81 | .18 | .21 | 160 | 47 | 102 | 5 | .29 |
| 7 | 2130 | 2.01 | .140 | 1.79 | .25 | .22 | 147 | 37 | 113 | 7 | .27 |
| 8 | 341 | 1.85 | .116 | 1.13 | .24 | .24 | 141 | 42 | 88 | 6 | .21 |
| 9 | 403 | 2.01 | .124 | 1.15 | .24 | .24 | 230 | 48 | 110 | 8 | .36 |
| 10 | 611 | 1.80 | .144 | 1.05 | .23 | .23 | 126 | 34 | 104 | 5 | .27 |
| 11 | 2560 | 2.90 | .160 | 0.90 | .22 | .28 | 186 | 34 | 108 | 6 | .32 |
| 12 | 468 | 1.79 | .104 | 1.43 | .22 | .23 | 150 | 36 | 109 | 6 | .32 |
| 13 | 482 | 1.94 | .116 | 1.64 | .21 | .26 | 130 | 35 | 158 | 7 | .34 |

TABLE 4-continued
ANALYSIS OF NEEDLES ON EACH ALDERIA AND MONDALE PINE TREE NOS. 1, 2 and 4–19 AFTER COMPLETION OF FOLIAR SPRAY TREATMENT SCHEDULE OF TABLE 2

| TREE NO. | $NO_3$—N | TOTAL % N | TOTAL % P | % K | % Na | % Mg | Mn ppm | Zn ppm | Fe ppm | Cu ppm | % Ca |
|---|---|---|---|---|---|---|---|---|---|---|---|
| 14 | 523 | 1.78 | .116 | 1.89 | .20 | .26 | 115 | 39 | 120 | 6 | .32 |
| 15 | 281 | 1.91 | .108 | 1.51 | .22 | .25 | 144 | 55 | 98 | 6 | .20 |
| 16 | 293 | 1.31 | .156 | 0.71 | .22 | .27 | 119 | 38 | 120 | 14 | .50 |
| 17 | 365 | 1.28 | .116 | 0.58 | .15 | .25 | 132 | 36 | 144 | 21 | .48 |
| 18 | 416 | 1.41 | .136 | 0.61 | .15 | .24 | 133 | 39 | 193 | 15 | .49 |
| 19 | 642 | 1.65 | .172 | 0.63 | .19 | .22 | 88 | 67 | 182 | 13 | .66 |

NOTES:
1. All percentages are weight percentages.

Having described my invention in such terms as to enable those skilled in the art to which it pertains to understand and practice it, and having described the presently preferred embodiments thereof, I claim:

1. A method for treating a stand of coniferous trees growing by natural processes and exposed to an atmosphere containing inorganic nitric acid or nitrate compounds to improve the resistance of said trees to damage by acid rain, said method comprising the step of foliarly applying at least one sugar selected from the group consisting of monosaccharides and disaccharides to said coniferous trees naturally growing in said stand exposed to said atmosphere.

* * * * *